(12) United States Patent
Gardner et al.

(10) Patent No.: US 8,486,615 B2
(45) Date of Patent: Jul. 16, 2013

(54) PHOTOPOLYMERIZABLE SILICONE MATERIALS FORMING SEMIPERMEABLE MEMBRANES FOR SENSOR APPLICATIONS

(75) Inventors: Geoffrey Bruce Gardner, Midland, MI (US); Sina Maghsoodi, Midland, MI (US); Brian Robert Harkness, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 1030 days.

(21) Appl. No.: 11/632,193

(22) PCT Filed: Jun. 21, 2005

(86) PCT No.: PCT/US2005/021768
§ 371 (c)(1),
(2), (4) Date: Jan. 17, 2007

(87) PCT Pub. No.: WO2006/023037
PCT Pub. Date: Mar. 2, 2006

(65) Prior Publication Data
US 2008/0277276 A1    Nov. 13, 2008

Related U.S. Application Data

(60) Provisional application No. 60/600,449, filed on Aug. 11, 2004.

(51) Int. Cl.
*G03C 1/74*    (2006.01)
(52) U.S. Cl.
USPC .......................... 430/496; 423/325; 205/793

(58) Field of Classification Search
USPC ................... 205/793; 204/415; 430/269, 496, 430/495.1; 423/325
See application file for complete search history.

(56) References Cited

U.S. PATENT DOCUMENTS

| 2,676,182 | A | | 4/1954 | Daudt et al. |
| 4,087,585 | A | | 5/1978 | Schulz |
| 4,503,208 | A | * | 3/1985 | Lin et al. .......................... 528/15 |
| 4,510,094 | A | | 4/1985 | Drahnak |

(Continued)

FOREIGN PATENT DOCUMENTS

| EP | 0493791 A1 | 12/1991 |
| EP | 0 497349 B1 | 6/1996 |

(Continued)

OTHER PUBLICATIONS

Chemistry of Materials, "Highly Active Visible-Light Photocatalysts for Curing a Ceramic Precursor," 1998, 10, pp. 531-536.

(Continued)

*Primary Examiner* — J. Christopher Ball
(74) *Attorney, Agent, or Firm* — Erika Takeuchi; Matthew T. Fewkes

(57) ABSTRACT

A method for preparing sensing devices (biosensors) includes the steps of: (1) applying a photopatternable silicone composition to a surface in a sensing device to form a film, (2) photopatterning the film by a process comprising exposing the film to radiation through a photomask without the use of a photoresist to produce an exposed film; (3) removing regions of the non-exposed film with a developing solvent to form a patterned film, which forms a permselective layer or an analyte attenuation layer covering preselected areas of the sensing device.

6 Claims, 2 Drawing Sheets

U.S. PATENT DOCUMENTS

| | | | |
|---|---|---|---|
| 4,530,879 | A | 7/1985 | Drahnak |
| 4,584,355 | A | 4/1986 | Blizzard et al. |
| 4,585,836 | A | 4/1986 | Homan et al. |
| 4,591,622 | A | 5/1986 | Blizzard et al. |
| 4,939,065 | A | 7/1990 | Cavezzan et al. |
| 5,063,081 | A | 11/1991 | Cozzette et al. |
| 5,145,886 | A | 9/1992 | Oxman et al. |
| 5,194,649 | A | 3/1993 | Okawa |
| 5,200,051 | A | 4/1993 | Cozzette et al. |
| 5,212,050 | A | 5/1993 | Mier et al. |
| 5,248,715 | A | 9/1993 | Gray et al. |
| 5,466,575 | A | 11/1995 | Cozzette et al. |
| 5,496,961 | A | 3/1996 | Dauth et al. |
| 5,554,339 | A | 9/1996 | Cozzette et al. |
| 5,744,507 | A | 4/1998 | Angel et al. |
| 5,837,446 | A | 11/1998 | Cozzette et al. |
| 5,837,454 | A | 11/1998 | Cozzette et al. |
| 6,001,943 | A | 12/1999 | Enami et al. |
| 6,046,250 | A | 4/2000 | Boardman et al. |
| 6,169,142 | B1 | 1/2001 | Nakano et al. |
| 6,306,594 | B1 | 10/2001 | Cozzette et al. |
| 6,323,253 | B1 | 11/2001 | Bennington |
| 6,531,260 | B2 | 3/2003 | Iwasawa et al. |
| 6,537,723 | B1 | 3/2003 | Toyoda et al. |
| 6,617,674 | B2 | 9/2003 | Becker et al. |
| 6,806,040 | B2 | 10/2004 | Toyoda et al. |
| 6,846,895 | B2 | 1/2005 | Iwasawa et al. |
| 6,905,904 | B2 | 6/2005 | Gardner et al. |
| 6,907,176 | B2 | 6/2005 | Gardner et al. |
| 6,933,097 | B2 | 8/2005 | Toyoda et al. |
| 6,991,887 | B1 | 1/2006 | Grate et al. |
| 7,358,582 | B2 | 4/2008 | Gardner et al. |
| 2003/0191268 | A1 | 10/2003 | Iwasawa et al. |

FOREIGN PATENT DOCUMENTS

| | | |
|---|---|---|
| EP | 1101167 A2 | 4/2006 |
| JP | 62294239 | 4/1987 |
| JP | 04-5658 | 1/1992 |
| JP | 10-212413 | 8/1998 |
| JP | 10-279884 | 10/1998 |
| JP | 10-319597 | 12/1998 |
| JP | 2000180643 | 6/2000 |
| JP | 2001288268 | 10/2001 |
| JP | 2004115460 | 4/2004 |
| JP | 2005531028 | 10/2005 |
| JP | 2005531029 | 10/2005 |
| JP | 2008506811 | 3/2008 |
| WO | 9210529 | 6/1992 |
| WO | WO 99/38003 | 7/1999 |
| WO | 0118121 | 3/2001 |
| WO | 0236652 | 5/2002 |
| WO | WO 02/36652 A2 * | 5/2002 |
| WO | 2004001458 | 12/2003 |
| WO | 2006019468 | 2/2006 |

OTHER PUBLICATIONS

H. Krassow, F. Campabadal, E. Lora-Tamayo, "Wafer level packaging of silicon pressure sensors," Sensors and Actuators 82 (2000), pp. 229-233.

* cited by examiner

PHOTOPOLYMERIZABLE SILICONE MATERIALS FORMING SEMIPERMEABLE MEMBRANES FOR SENSOR APPLICATIONS

CROSS REFERENCE TO RELATED APPLICATIONS

This application is a U.S. national stage filing under 35 U.S.C. §371 of PCT Application No. PCT/US05/021768 filed on 21 Jun. 2005, currently pending, which claims the benefit of U.S. Provisional Patent Application No. 60/600,449 filed 11 Aug. 2004 under 35 U.S.C. §119 (e). PCT Application No. PCT/US05/021768 and U.S. Provisional Patent Application No. 60/600,449 are hereby incorporated by reference.

TECHNICAL FIELD

This invention relates to methods for forming semipermeable membranes useful as permselective layers and analyte attenuation layers in sensing devices. This invention further relates to sensing devices including the semipermeable membranes.

BACKGROUND

Thin film silicone rubbers and silicone-organic copolymers are finding increasing use in a wide array of sensing devices and other microelectronic devices packaged using standard semiconductor methodologies. One class of devices incorporating silicone-based materials is microassay sensing devices in which the silicone-based materials function as semipermeable membranes. Devices have been constructed whereby a silicone-based material overcoats the active region of a sensor, forming a semipermeable membrane between the sensor and the environment. The intrinsic selectivity and permeability of the silicone-based material regulates the flow of molecules to the active portion of the sensor and allows for a response of the sensor to only the desired analyte. In this way, analyte specific sensors can be constructed that can be used for chemically complex samples (such as blood, urine, or other biological samples) with a reduced observance of false responses.

One difficulty with incorporation of silicone-based materials in such a sensing device is the inability to directly pattern the films. In building the semipermeable membrane on the sensor, patterning of the silicone-based materials has traditionally required a multistep process where a patterning agent (such as a photoresist) is coated over the silicone-based film, the photoresist is dried, the photoresist is exposed to UV irradiation through a photomask, the patterned photoresist is developed, the selectively exposed underlayer of silicone-based material is solvent developed, and the remaining photoresist is stripped off. These processing steps to pattern the silicone-based material add complexity and cost to the process, require several material handling steps, and can frequently be identified as the source of device yield reduction.

Problem to be Solved by this Invention

Therefore, a continuing need exists to simplify the processing steps to produce sensing devices.

Means for Solving the Problem

Photopatternable silicone compositions are used to prepare semipermeable membranes for sensor applications. These photopatternable silicone compositions can be patterned without the use of photoresists (or equivalent patterning agents). Processing of films of photopatternable silicone compositions can be accomplished by direct exposure of the film to UV light through a photomask, optionally heating of the film to induce cure, and solvent development.

SUMMARY

This invention relates to a method for forming a semipermeable membrane, such as a permselective membrane or analyte attenuation layer, in a sensing device and the device formed therefrom. The method comprises:

(1) applying a photopatternable silicone composition to a surface in a sensing device to form a film, (2) photopatterning the film by a process comprising exposing the film to radiation through a photomask without using a photoresist to produce an exposed film;

(3) removing regions of the non-exposed film with a developing solvent to form a patterned film.

DETAILED DESCRIPTION

All amounts ratios and percentages are by weight, unless otherwise indicated. The following is a list of definitions, as used herein.

"M" means a siloxane unit of formula $R_3SiO_{1/2}$, where R is a monovalent organic group.

"D" means a siloxane unit of formula $R_2SiO_{2/2}$, where R is a monovalent organic group.

"T" means a siloxane unit of formula $RSiO_{3/2}$, where R is a monovalent organic group.

"Q" means a siloxane unit of formula $SiO_{4/2}$, where R is a monovalent organic group.

When introducing elements of this invention, the articles "a", "an", and "the" mean that there are one or more of the elements. The terms "comprising", "including", and "having" mean that there may be additional elements other than the named elements.

Photopatternable Silicone Compositions

Suitable photopatternable silicone compositions are known in the art and commercially available. Suitable photopatternable silicone compositions are exemplified by photopatternable hydrosilylation curable silicone compositions and photopatternable silicone resin compositions. Suitable photopatternable hydrosilylation curable silicone compositions are disclosed in, for example, U.S. Pat. No. 6,617,674, which is hereby incorporated by reference.

An example of a photopatternable hydrosilylation curable silicone composition suitable for use in this invention comprises:

(A) an organopolysiloxane containing an average of at least two silicon-bonded unsaturated organic groups per molecule, (B) an organosilicon compound containing an average of at least two silicon-bonded hydrogen atoms per molecule in a concentration sufficient to cure the composition, and (C) a catalytic amount of a photoactivated hydrosilylation catalyst.

Component (A)

Component (A) comprises at least one organopolysiloxane containing, per molecule, an average of at least two silicon-bonded unsaturated organic groups capable of undergoing a hydrosilylation reaction, such as alkenyl groups. The organopolysiloxane may have a linear, branched, or resinous structure. The organopolysiloxane may be a homopolymer or a copolymer. The unsaturated organic groups may have 2 to 10 carbon atoms and are exemplified by, but not limited to, alkenyl groups such as vinyl, allyl, butenyl, and hexenyl. The unsaturated organic groups in the organopolysiloxane may be located at terminal, pendant, or both terminal and pendant positions.

The remaining silicon-bonded organic groups in the organopolysiloxane are organic groups free of aliphatic unsaturation. These organic groups may be independently selected from monovalent hydrocarbon and monovalent halogenated hydrocarbon groups free of aliphatic unsaturation. These monovalent groups may have from 1 to 20 carbon atoms, alternatively 1 to 10 carbon atoms, and are exemplified by, but not limited to alkyl such as methyl, ethyl, propyl, pentyl, octyl, undecyl, and octadecyl; cycloalkyl such as cyclohexyl; aryl such as phenyl, tolyl, xylyl, benzyl, and 2-phenylethyl; and halogenated hydrocarbon groups such as 3,3,3-trifluoropropyl, 3-chloropropyl, and dichlorophenyl. At least 50 percent, alternatively at least 80%, of the organic groups free of aliphatic unsaturation in the organopolysiloxane may be methyl.

The viscosity of the organopolysiloxane at 25° C. varies with molecular weight and structure, but may be 0.001 to 100,000 Pascal·seconds (Pa·s), alternatively 0.01 to 10,000 Pa·s, and alternatively 0.01 to 1,000 Pa·s.

Examples of organopolysiloxanes useful in the photopatternable hydrosilylation curable silicone composition include, but are not limited to, polydiorganosiloxanes having the following formulae: $ViMe_2SiO(Me_2SiO)_aSiMe_2Vi$, $ViMe_2SiO(Me_2SiO)_{0.25a}(MePhSiO)_{0.75a}SiMe_2Vi$, $ViMe_2SiO(Me_2SiO)_{0.95a}(Ph2SiO)_{0.05a}SiMe_2Vi$, $ViMe_2SiO(Me_2SiO)_{0.98a}(MeViSiO)_{0.02a}SiMe_2Vi$, $Me_3SiO(Me_2SiO)_{0.95a}(MeViSiO)_{0.05a}SiMe_3$, and $PhMeViSiO(Me_2SiO)_a SiPhMeVi$, where Me, Vi, and Ph denote methyl, vinyl, and phenyl respectively and subscript a has a value such that the viscosity of the polydiorganosiloxane is 0.001 to 100,000 Pa·s.

Methods of preparing organopolysiloxanes suitable for use in the photopatternable hydrosilylation curable silicone composition, such as hydrolysis and condensation of the corresponding organohalosilanes or equilibration of cyclic polydiorganosiloxanes, are known in the art.

Examples of organopolysiloxane resins include an MQ resin consisting essentially of $R^1_3SiO_{1/2}$ units and $SiO_{4/2}$ units, a TD resin consisting essentially of $R^1SiO_{3/2}$ units and $R^1_2SiO_{2/2}$ units, an MT resin consisting essentially of $R^1_3SiO_{1/2}$ units and $R^1SiO_{3/2}$ units, and an MTD resin consisting essentially of $R^1_3SiO_{1/2}$ units, $R^1SiO_{3/2}$ units, and $R^1_2SiO_{2/2}$ units, wherein each $R^1$ is independently selected from monovalent hydrocarbon and monovalent halogenated hydrocarbon groups. The monovalent groups represented by $R^1$ may have 1 to 20 carbon atoms, alternatively 1 to 10 carbon atoms.

Examples of monovalent groups for $R^1$ include, but are not limited to, alkyl such as methyl, ethyl, propyl, pentyl, octyl, undecyl, and octadecyl; cycloalkyl such as cyclohexyl; alkenyl such as vinyl, allyl, butenyl, and hexenyl; aryl such as phenyl, tolyl, xylyl, benzyl, and 2-phenylethyl; and halogenated hydrocarbon groups such as 3,3,3-trifluoropropyl, 3-chloropropyl, and dichlorophenyl. At least one-third, and alternatively substantially all $R^1$ groups in the organopolysiloxane resin may be methyl. An exemplary organopolysiloxane resin consists essentially of $(CH_3)_3SiO_{1/2}$ siloxane units and $SiO_{4/2}$ where the mole ratio of $(CH_3)_3SiO_{1/2}$ units to $SiO_{4/2}$ units is 0.6 to 1.9.

The organopolysiloxane resin may contain an average of 3 to 30 mole percent of unsaturated organic groups capable of undergoing a hydrosilylation reaction, such as alkenyl groups. The mole percent of unsaturated organic groups in the resin is the ratio of the number of moles of unsaturated organic group-containing siloxane units in the resin to the total number of moles of siloxane units in the resin, multiplied by 100.

The organopolysiloxane resin may be prepared by methods known in the art. For example, the organopolysiloxane resin may prepared by treating a resin copolymer produced by the silica hydrosol capping process of Daudt et al. with at least an alkenyl-containing endblocking reagent. The method of Daudt et al., is disclosed in U.S. Pat. No. 2,676,182.

Briefly stated, the method of Daudt et al. involves reacting a silica hydrosol under acidic conditions with a hydrolyzable triorganosilane such as trimethylchlorosilane, a siloxane such as hexamethyldisiloxane, or combinations thereof, and recovering a copolymer having M and Q units. The resulting copolymers may contain 2 to 5 percent by weight of hydroxyl groups.

The organopolysiloxane resin, which may contain less than 2 percent by weight of silicon-bonded hydroxyl groups, may be prepared by reacting the product of Daudt et al. with an alkenyl-containing endblocking agent or a mixture of an alkenyl-containing endblocking agent and an endblocking agent free of aliphatic unsaturation in an amount sufficient to provide 3 to 30 mole percent of alkenyl groups in the final product. Examples of endblocking agents include, but are not limited to, silazanes, siloxanes, and silanes. Suitable endblocking agents are known in the art and are exemplified in U.S. Pat. Nos. 4,584,355; 4,591,622; and 4,585,836. A single endblocking agent or a mixture of endblocking agents may be used to prepare the organopolysiloxane resin.

Component (A) may be a single organopolysiloxane or a combination comprising two or more organopolysiloxanes that differ in at least one of the following properties: structure, viscosity, average molecular weight, siloxane units, and sequence.

Component (B)

Component (B) is at least one organosilicon compound containing an average of at least two silicon-bonded hydrogen atoms per molecule. It is generally understood that crosslinking occurs when the sum of the average number of alkenyl groups per molecule in component (A) and the average number of silicon-bonded hydrogen atoms per molecule in component (B) is greater than four. The silicon-bonded hydrogen atoms in the organohydrogenpolysiloxane may be located at terminal, pendant, or at both terminal and pendant positions.

The organosilicon compound may be an organosilane or an organohydrogensiloxane. The organosilane may be a monosilane, disilane, trisilane, or polysilane. Similarly, the organohydrogensiloxane may be a disiloxane, trisiloxane, or polysiloxane. The organosilicon compound may an organohydrogensiloxane or the organosilicon compound may be an organohydrogenpolysiloxane. The structure of the organosilicon compound may be linear, branched, cyclic, or resinous. At least 50 percent of the organic groups in the organosilicon compound may be methyl.

Examples of organosilanes include, but are not limited to, monosilanes such as diphenylsilane and 2-chloroethylsilane; disilanes such as 1,4-bis(dimethylsilyl)benzene, bis[(p-dimethylsilyl)phenyl]ether, and 1,4-dimethyldisilylethane; trisilanes such as 1,3,5-tris(dimethylsilyl)benzene and 1,3,5-trimethyl-1,3,5-trisilane; and polysilanes such as poly(methylsilylene)phenylene and poly(methylsilylene)methylene.

Examples of organohydrogensiloxanes include, but are not limited to, disiloxanes such as 1,1,3,3-tetramethyldisiloxane and 1,1,3,3-tetraphenyldisiloxane; trisiloxanes such as phenyltris(dimethylsiloxy)silane and 1,3,5-trimethylcyclotrisiloxane; and polysiloxanes such as a trimethylsiloxy-terminated poly(methylhydrogensiloxane), a trimethylsiloxy-terminated poly(dimethylsiloxane/methylhydrogensiloxane), a dimethylhydrogensiloxy-terminated poly(methylhydrogensiloxane), and a resin consisting essentially of $H(CH_3)_2SiO_{1/2}$ units, $(CH_3)_3SiO_{1/2}$ units, and $SiO_{4/2}$ units.

Component (B) may be a single organosilicon compound or a combination comprising two or more such compounds that differ in at least one of the following properties: structure, average molecular weight, viscosity, silane units, siloxane units, and sequence.

The concentration of component (B) in the photopatternable hydrosilylation curable silicone composition of the present invention is sufficient to cure (crosslink) the composition. The exact amount of component (B) depends on the desired extent of cure, which generally increases as the ratio of the number of moles of silicon-bonded hydrogen atoms in component (B) to the number of moles of unsaturated organic groups in component (A) increases. The concentration of component (B) may be sufficient to provide from 0.5 to 3 silicon-bonded hydrogen atoms per alkenyl group in component (A). Alternatively, the concentration of component (B) is sufficient to provide 0.7 to 1.2 silicon-bonded hydrogen atoms per alkenyl group in component (A).

Methods of preparing organosilicon compounds containing silicon-bonded hydrogen atoms are known in the art. For example, organopolysilanes may be prepared by reaction of chlorosilanes in a hydrocarbon solvent in the presence of sodium or lithium metal (Wurtz reaction). Organopolysiloxanes may be prepared by hydrolysis and condensation of organohalosilanes.

To ensure compatibility of components (A) and (B), the predominant organic group in each component may be the same.

Component (C)

Component (C) is a photoactivated hydrosilylation catalyst. The photoactivated hydrosilylation catalyst may be any hydrosilylation catalyst capable of catalyzing the hydrosilylation of component (A) with component (B) upon exposure to radiation having a wavelength of from 150 to 800 nanometers (nm) and subsequent heating. The platinum group metals include platinum, rhodium, ruthenium, palladium, osmium and iridium. The platinum group metal may be platinum due to its high activity in hydrosilylation reactions. The suitability of particular photoactivated hydrosilylation catalyst for use in the photopatternable hydrosilylation curable silicone composition may be determined by routine experimentation using the methods in the Examples section below.

Examples of photoactivated hydrosilylation catalysts include, but are not limited to, platinum(II) b-diketonate complexes such as platinum(II) bis(2,4-pentanedioate), platinum (II) bis(2,4-hexanedioate), platinum(II) bis(2,4-heptanedioate), platinum(II) bis(1-phenyl-1,3-butanedioate, platinum (II) bis(1,3-diphenyl-1,3-propanedioate), platinum(II) bis(1, 1,1,5,5,5-hexafluoro-2,4-pentanedioate); (h-cyclopentadienyl)trialkylplatinum complexes, such as (Cp)trimethylplatinum, (Cp)ethyldimethylplatinum, (Cp)triethylplatinum, (chloro-Cp)trimethylplatinum, and (trimethylsilyl-Cp)trimethylplatinum, where Cp represents cyclopentadienyl; triazene oxide-transition metal complexes, such as $Pt[C_6H_5NNNOCH_3]_4$, $Pt[p-CN—C_6H_4NNNOC_6H_{11}]_4$, $Pt[p-H_3COC_6H_4NNNOC_6H_{11}]_4$, $Pt[p—CH_3(CH_2)b-C_6H_4NNNOCH_3]_4$, 1,5-cyclooctadiene.Pt[p-CN—$C_6H_4NNNOC_6H_{11}]_2$, 1,5-cyclooctadiene.Pt[p—$CH_3O—C_6H_4NNNOCH_3]_2$, $[(C_6H_5)_3P]_3Rh[p-CN—C_6H_4NNNOC_6H_{11}]$, and $Pd[p—CH_3(CH_2)b—C_6H_4NNNOCH_3]_2$, where b is 1, 3, 5, 11, or 17; (η-diolefin)(σ-aryl)platinum complexes, such as (η$^4$-1,5-cyclooctadienyl)diphenylplatinum, h4-1,3,5,7-cyclooctatetraenyl)diphenylplatinum, (η$^4$-2,5-norboradienyl)diphenylplatinum, (η$^4$-1,5-cyclooctadienyl) bis-(4-dimethylaminophenyl)platinum, (η$^4$-1,5-cyclooctadienyl)bis-(4-acetylphenyl)platinum, and (η$^4$-1,5-cyclooctadienyl)bis-(4-trifluormethylphenyl)platinum. Alternatively, the photoactivated hydrosilylation catalyst is a Pt(II) b-diketonate complex, and alternatively the catalyst is platinum(II) bis(2,4-pentanedioate).

Component (C) may be a single photoactivated hydrosilylation catalyst or a combination comprising two or more such catalysts.

The concentration of component (C) is sufficient to catalyze the hydrosilylation reaction of components (A) and (B) upon exposure to radiation and heat in the method described herein. The concentration of component (C) may be sufficient to provide 0.1 to 1000 parts per million (ppm) of platinum group metal, alternatively 0.5 to 100 ppm of platinum group metal, alternatively 1 to 25 ppm of platinum group metal, based on the combined weight of components (A), (B), and (C). The rate of cure may be slow below 1 ppm of platinum group metal. The use of more than 100 ppm of platinum group metal may result in no appreciable increase in cure rate, which would be uneconomical.

Methods of preparing the photoactivated hydrosilylation catalysts are known in the art. For example, methods of preparing platinum(II) β-diketonates are reported by Guo et al. (Chemistry of Materials, 1998, 10, 531-536). Methods of preparing (η-cyclopentadienyl)trialkylplatinum complexes and are disclosed in U.S. Pat. No. 4,510,094. Methods of preparing triazene oxide-transition metal complexes are disclosed in U.S. Pat. No. 5,496,961. Methods of preparing (η-diolefin)(σ-aryl)platinum complexes are disclosed in U.S. Pat. No. 4,530,879.

Optional Components

The photopatternable hydrosilylation curable silicone composition may further comprise one or more optional components, provided the optional component does not adversely affect the photopatterning or cure of the composition in the method of this invention. Examples of optional components include, but are not limited to, (D) an inhibitor, (E) a filler, (F) a treating agent for the filler, (G) a vehicle, (H) a spacer, (I) an adhesion promoter, (J) a surfactant, (K) a photosensitizer, (L) colorants such as a pigment or dye, and combinations thereof.

Component (D)

Combinations of components (A), (B), and (C) may begin to cure at ambient temperature. To obtain a longer working time or "pot life", the activity of the catalyst under ambient conditions may be retarded or suppressed by the addition of (D) an inhibitor to the photopatternable hydrosilylation curable silicone composition. A platinum group catalyst inhibitor retards curing of the present photopatternable hydrosilylation curable silicone composition at ambient temperature, but does not prevent the composition from curing at elevated temperatures. Suitable platinum catalyst inhibitors include various "ene-yne" systems such as 3-methyl-3-penten-1-yne and 3,5-dimethyl-3-hexen-1-yne; acetylenic alcohols such as 3,5-dimethyl-1-hexyn-3-ol, 1-ethynyl-1-cyclohexanol, and 2-phenyl-3-butyn-2-ol; maleates and fumarates, such as the well known dialkyl, dialkenyl, and dialkoxyalkyl fumarates and maleates; and cyclovinylsiloxanes.

The concentration of platinum catalyst inhibitor in the photopatternable hydrosilylation curable silicone composition is sufficient to retard curing of the composition at ambient temperature without preventing or excessively prolonging cure at elevated temperatures. This concentration will vary depending on the particular inhibitor used, the nature and concentration of the hydrosilylation catalyst, and the nature of the organohydrogenpolysiloxane. However, inhibitor concentrations as low as one mole of inhibitor per mole of platinum group metal may yield a satisfactory storage stability and cure rate. Inhibitor concentrations of up to 500 or more moles of inhibitor per mole of platinum group metal may be used. One skilled in the art would be able to determine the optimum concentration for a particular inhibitor in a particular silicone composition by routine experimentation.

Component (E)

Component (E) is a filler. Component (E) may comprise a thermally conductive filler, a reinforcing filler, or combinations thereof. The thermally conductive filler may be thermally conductive, electrically conductive, or both. Alternatively, component (E) may be thermally conductive and electrically insulating. Suitable thermally conductive fillers for component (E) include metal particles, metal oxide particles, and a combination thereof. Suitable thermally conductive fillers for component (E) are exemplified by aluminum nitride; aluminum oxide; barium titanate; beryllium oxide; boron nitride; diamond; graphite; magnesium oxide; metal particulate such as copper, gold, nickel, or silver; silicon carbide; tungsten carbide; zinc oxide, and combinations thereof.

Thermally conductive fillers are known in the art and commercially available, see for example, U.S. Pat. No. 6,169,142 (col. 4, lines 7-33). For example, CB-A20S and Al-43-Me are aluminum oxide fillers of differing particle sizes commercially available from Showa-Denko, and AA-04, AA-2, and AA18 are aluminum oxide fillers commercially available from Sumitomo Chemical Company.

Silver filler is commercially available from Metalor Technologies U.S.A. Corp. of Attleboro, Mass., U.S.A. Boron nitride filler is commercially available from Advanced Ceramics Corporation, Cleveland, Ohio, U.S.A.

Reinforcing fillers include silica, and chopped fiber, such as chopped KEVLAR®.

A combination of fillers having differing particle sizes and different particle size distributions may be used as component (E). For example, it may be desirable to combine a first filler having a larger average particle size with a second filler having a smaller average particle size in a proportion meeting the closest packing theory distribution curve. This improves packing efficiency and may reduce viscosity and enhance heat transfer.

Component (F)

The filler for component (E) may optionally be surface treated with component (F) a treating agent. Treating agents and treating methods are known in the art, see for example, U.S. Pat. No. 6,169,142 (col. 4, line 42 to col. 5, line 2).

The treating agent may be an alkoxysilane having the formula: $R^3{}_c Si(OR^4)_{(4-c)}$, where c is 1, 2, or 3; alternatively c is 3. $R^3$ is a substituted or unsubstituted monovalent hydrocarbon group of at least 1 carbon atom, alternatively at least 8 carbon atoms. R3 has up to 50 carbon atoms, alternatively up to 30 carbon atoms, alternatively up to 18 carbon atoms. $R^3$ is exemplified by alkyl groups such as hexyl, octyl, dodecyl, tetradecyl, hexadecyl, and octadecyl; and aromatic groups such as benzyl, phenyl and phenylethyl. $R^3$ may be saturated or unsaturated, branched or unbranched, and unsubstituted. $R^3$ may be saturated, unbranched, and unsubstituted.

$R^4$ is an unsubstituted, saturated hydrocarbon group of at least 1 carbon atom. $R^4$ may have up to 4 carbon atoms, alternatively up to 2 carbon atoms. Component C) is exemplified by hexyltrimethoxysilane, octyltriethoxysilane, decyltrimethoxysilane, dodecyltrimethyoxysilane, tetradecyltrimethoxysilane, phenyltrimethoxysilane, phenylethyltrimethoxysilane, octadecyltrimethoxysilane, octadecyltriethoxysilane, a combination thereof, and others.

Alkoxy-functional oligosiloxanes may also be used as treatment agents. Alkoxy-functional oligosiloxanes and methods for their preparation are known in the art, see for example, EP 1 101 167 A2. For example, suitable alkoxy-functional oligosiloxanes include those of the formula $(R^7O)_d Si(OSiR^5{}_2R^6)_{4-d}$. In this formula, d is 1, 2, or 3, alternatively d is 3. Each $R^5$ is may be independently selected from saturated and unsaturated monovalent hydrocarbon groups of 1 to 10 carbon atoms. Each $R^6$ may be a saturated or unsaturated monovalent hydrocarbon group having at least 11 carbon atoms. Each $R^7$ may be an alkyl group.

Metal fillers may be treated with alkylthiols such as octadecyl mercaptan and others, and fatty acids such as oleic acid, stearic acid, titanates, titanate coupling agents, zirconate coupling agents, a combination thereof, and others.

Treatment agents for alumina or passivated aluminum nitride could include alkoxysilyl functional alkylmethyl polysiloxanes (e.g., partial hydrolysis condensate of $R^8{}_e R^9{}_f Si(OR^{10})_{(4-e-f)}$ or cohydrolysis condensates or mixtures), similar materials where the hydrolyzable group would be silazane, acyloxy or oximo. In all of these, a group tethered to Si, such as $R^8$ in the formula above, is an unsaturated monovalent hydrocarbon or monovalent aromatic-functional hydrocarbon. $R^9$ is a monovalent hydrocarbon group, and $R^{10}$ is a monovalent hydrocarbon group of 1 to 4 carbon atoms. In the formula above, e is 1, 2, or 3 and f is 0, 1, or 2, with the proviso that e+f is 1, 2, or 3. One skilled in the art could optimize a specific treatment to aid dispersion of the filler by routine experimentation.

Component (G)

Component (G) is a vehicle such as a solvent or diluent. Component (G) may be added during preparation of the photopatternable hydrosilylation curable silicone composition, for example, to aid mixing and delivery. All or a portion of component (G) may optionally be removed after the photopatternable hydrosilylation curable silicone composition is prepared or applied to a substrate. One skilled in the art could determine the optimum concentration of a particular vehicle in the photopatternable hydrosilylation curable silicone composition by routine experimentation.

Component (G) may comprise at least one organic solvent to lower the viscosity of the composition and facilitate the preparation, handling, or application of the composition. The choice of solvent is governed by many factors such as the solubility and miscibility of the components in the composition, the process for applying the photopatternable silicone composition, and safety and environmental regulations. Examples of suitable solvents include, but are not limited to, ether-, ester-, hydroxyl- and ketone-containing compounds; saturated hydrocarbons having from 1 to 20 carbon atoms; aromatic hydrocarbons such as xylenes and mesitylene; mineral spirits; halohydrocarbons; silicone fluids such as linear, branched, and cyclic polydimethylsiloxanes; and combinations thereof. Examples of suitable solvents include, but are not limited to, cyclohexanone, cyclopentanone, lactate esters, alkylene glycol alkyl ether esters, such as propylene glycol methyl ether acetate (PGMEA), methyl isobutyl ketone (MIBK), ethyl lactate (EL), methyl ethyl ketone (MEK), 2-heptanone, 3-methoxy-3 methyl-1-butanol (MMB), and combinations thereof. The amount of solvent used may be 40 to 90% based on the total amount of composition, alternatively the amount of solvent may be 50 to 70%.

Component (H)

Component (H) is a spacer. Spacers may comprise organic particles, inorganic particles, or a combination thereof. Spacers may be thermally conductive, electrically conductive, or both. Spacers may have a particle size of at least 25 micrometers up to 250 micrometers. Spacers may comprise monodisperse beads. Spacers are exemplified by, but not limited to, polystyrene, glass, perfluorinated hydrocarbon polymers, and combinations thereof. Spacers may be added in addition to, or instead of, all or a portion of the filler.

Component (I)

Component (I) is an adhesion promoter. Component (I) may comprise a transition metal chelate, an alkoxysilane, a combination of an alkoxysilane and a hydroxy-functional polyorganosiloxane, or a combination thereof.

Component (I) may be an unsaturated or epoxy-functional compound. Suitable epoxy-functional compounds are known in the art and commercially available, see for example, U.S. Pat. Nos. 4,087,585; 5,194,649; 5,248,715; and 5,744,507 col. 4-5. Component (I) may comprise an unsaturated or epoxy-functional alkoxysilane. For example, the functional alkoxysilane may have the formula $R^{11}{}_g Si(OR^{12})_{(4-g)}$, where g is 1, 2, or 3, alternatively g is 1.

Each $R^{11}$ is independently a monovalent organic group with the proviso that at least one $R^{11}$ is an unsaturated organic group or an epoxy-functional organic group. Epoxy-functional organic groups for $R^{11}$ are exemplified by 3-glycidoxypropyl and (epoxycyclohexyl)ethyl. Unsaturated organic groups for $R^{11}$ are exemplified by 3-methacryloyloxypropyl, 3-acryloyloxypropyl, and unsaturated monovalent hydrocarbon groups such as vinyl, allyl, hexenyl, undecylenyl.

Each $R^{12}$ is independently an unsubstituted, saturated hydrocarbon group of at least 1 carbon atom. $R^{12}$ may have up to 4 carbon atoms, alternatively up to 2 carbon atoms. $R^{12}$ is exemplified by methyl, ethyl, propyl, and butyl.

Examples of suitable epoxy-functional alkoxysilanes include 3-glycidoxypropyltrimethoxysilane, 3-glycidoxypropyltriethoxysilane, (epoxycyclohexyl)ethyldimethoxysilane, (epoxycyclohexyl)ethyldiethoxysilane and combinations thereof. Examples of suitable unsaturated alkoxysilanes include vinyltrimethoxysilane, allyltrimethoxysilane, allyltriethoxysilane, hexenyltrimethoxysilane, undecylenyltrimethoxysilane, 3-methacryloyloxypropyl trimethoxysilane, 3-methacryloyloxypropyl triethoxysilane, 3-acryloyloxypropyl trimethoxysilane, 3-acryloyloxypropyl triethoxysilane, and combinations thereof.

Component (I) may comprise an epoxy-functional siloxane such as a reaction product of a hydroxy-terminated polyorganosiloxane with an epoxy-functional alkoxysilane, as described above, or a physical blend of the hydroxy-terminated polyorganosiloxane with the epoxy-functional alkoxysilane. Component (I) may comprise a combination of an epoxy-functional alkoxysilane and an epoxy-functional siloxane. For example, component (I) is exemplified by a mixture of 3-glycidoxypropyltrimethoxysilane and a reaction product of hydroxy-terminated methylvinylsiloxane with 3-glycidoxypropyltrimethoxysilane, or a mixture of 3-glycidoxypropyltrimethoxysilane and a hydroxy-terminated methylvinylsiloxane, or a mixture of 3-glycidoxypropyltrimethoxysilane and a hydroxy-terminated methylvinyl/dimethylsiloxane copolymer. When used as a physical blend rather than as a reaction product, these components may be stored separately in multiple-part kits.

Suitable transition metal chelates include titanates, zirconates such as zirconium acetylacetonate, aluminum chelates such as aluminum acetylacetonate, and combinations thereof. Transition metal chelates and methods for their preparation are known in the art, see for example, U.S. Pat. No. 5,248,715, EP 0 493 791 A1, and EP 0 497 349 B1.

The photopatternable hydrosilylation curable silicone composition of this invention may be a one-part composition comprising components (A) through (C) and optionally one or more of components (D) through (I) in a single part or, alternatively, a multi-part composition comprising components (A) through (C) and optionally one or more of components (D) through (I) in two or more parts. In a multi-part composition, components (A), (B), and (C) are typically not present in the same part unless an inhibitor is also present. For example, a multi-part photopatternable hydrosilylation curable silicone composition may comprise a first part containing a portion of component (A) and a portion of component (B) and optionally one or more of components (D) through (I), and a second part containing the remaining portion of component (A) and all of component (C) and optionally one or more of components (D) through (I).

The one-part photopatternable hydrosilylation curable silicone composition of the instant invention may be prepared by combining components (A) through (C) and optionally one or more of components (D) through (I) in the stated proportions at ambient temperature with or without the aid of a vehicle, which is described above. Although the order of addition of the various components is not critical if the photopatternable hydrosilylation curable silicone composition is to be used immediately, component (C) may be added last at a temperature below 30° C. to prevent premature curing of the composition. The multi-part photopatternable hydrosilylation curable silicone composition of the present invention may be prepared by combining the particular components designated for each part.

When a multi-part composition is prepared, it may be marketed as a kit. The kit may further comprise information or instructions or both as how to use the kit, how to combine the parts, or how to cure the resulting combination, or combinations thereof.

Alternatively, the photopatternable silicone composition may be a photopatternable silicone resin composition. A photopatternable silicone resin composition suitable for use in this invention comprises:

(a) a curable silicone resin and
(b) a photoinitiator.

Component (a) Curable Silicone Resin

Curable silicone resins suitable for use in this invention may include any curable silicone resin that is photopatternable. Curable silicone resins may comprise M, D, T, Q, and combinations thereof. Curable silicone resins may comprise MQ resins, DT resins, or TT resins, and combinations thereof. One skilled in the art would be able to prepare suitable silicone resins without undue experimentation by, for example, varying appropriate starting materials in the methods of Daudt, et al., described above. Component (a) may be selected from an acrylic functional silicone resin, a vinyl ether functional silicone resin, an epoxy functional silicone resin, or a combination thereof.

Acrylic Functional Silicone Resin

The acrylic functional silicone resin may comprise units of the formulae: $(CH_2=CR^{13}COOR^{14})SiO_{3/2}$ and $R^{15}SiO_{3/2}$, where each $R^{13}$ is independently a hydrogen atom or methyl group, each $R^{14}$ is independently a hydrocarbylene group having 1 to 8 carbon atoms, and each $R^{15}$ is independently an alkyl, cyclic alkyl, aryl or alkenyl group having 1 to 8 carbon atoms.

$R^{14}$ is exemplified by, but not limited to, methylene, ethylene, propylene, arylene groups and alkenylene groups. $R^{15}$ is exemplified by, but not limited to, methyl, ethyl, propyl, hexyl, octyl, vinyl, allyl, hexenyl, cyclohexyl, 2-cyclohexylethyl, 3,3,3-trifluoropropyl, phenyl, and naphthyl. Alternatively, $R^{15}$ is exemplified by, but not limited to, methyl, phenyl and combinations thereof. Alternatively, each $R^{15}$ is phenyl.

An example of such an acrylic functional silicone resin has the formula:

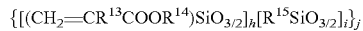

where $R^{13}$, $R^{14}$, and $R^{15}$ are as described above, $0.05 < h < 0.95$, $0.05 < i < 0.95$, provided that $h+i$ is 1. Alternatively, h is 0.3 to 0.45 and i is 0.55 to 0.7. The acrylic functional silicone resin has j being a value sufficient to give the acrylic functional silicone resin a weight average molecular weight (Mw) of 3,000 to 100,000 grams per mole (g/mol) in terms of polystyrene by gel permeation chromatography (GPC).

Examples of the acrylic functional silicone resins include poly(phenyl-co-(meth)acryloxypropyl)silsesquioxanes, which may be synthesized by co-hydrolyzing phenyltrimethoxysilane and 3-acryloxypropyltrimethoxysilane or 3-methacryloxypropyltrimethoxysilane. Examples of poly(phenyl-co-(meth)acryloxypropyl)silsesquioxane resins include: poly(phenyl-co-3-acryloxypropyl)silsesquioxane having the unit formula $T(Ph)_{0.67}T(acryloxy\ propyl)_{0.33}$ and poly(phenyl-co-3-methacryloxypropyl)silsesquioxane having a unit formula selected from the group consisting of: $T(Ph)_{0.67}\ T(methacryloxy\ propyl)_{0.33}$, $T(Phenyl)_{0.90}\ T(methacryloxy\ propyl)_{0.10}$, and $T(Phenyl)_{0.50}\ T(methacryloxy\ propyl)_{0.50}$. ("Ph" represents a phenyl group.)

The acrylic functional silicone resins can be prepared by co-hydrolyzing a trialkoxysilane having the formula $R^{15}Si(OR^{16})_3$ or a trichlorosilane having the formula $R^{15}SiCl_3$ with a acryloxy functional trialkoxysilane having the formula $(CH_2=CR^{13}COOR^{14})Si(OR^{16})_3$ or a trichlorosilane having the formula $(CH_2=CR^{13}COOR^{14})SiCl_3$, where $R^{14}$, $R^{13}$ and $R^{15}$ are defined as above and each $R^{16}$ is independently an alkyl group having 1 to 3 carbon atoms. $R^{16}$ is exemplified by methyl, ethyl and propyl. Alternatively, each $R^{16}$ is methyl.

Examples of trialkoxysilanes include, but are not limited to, methyltrimethoxysilane, ethyltrimethoxysilane, methyltriethoxysilane, ethyltriethoxysilane, phenyltrimethoxysilane, and phenyltriethoxysilane.

Examples of acryloxy functional trialkoxysilanes, include but are not limited to, acryloxypropyltrimethoxysilane, acryloxypropyltriethoxysilane, (2-methyl) acryloxypropyltrimethoxysilane, and (2-methyl) acryloxypropyltriethoxysilane.

The co-hydrolysis of the alkoxysilanes may be performed in the presence of a base catalyst. Suitable base catalysts include conventionally known inorganic bases and organic bases. An inorganic and organic base such as potassium hydroxide (KOH), cesium hydroxide (CsOH), ammonium hydroxide (NH$_4$OH), tetramethyl ammonium hydroxide (TMAH), tetrabutylammonium hydroxy (TBAH), and phosphazene bases, such as Phosphazene Base $P_4$-t-butyl solution. The amount of base catalyst used may be 0.001 to 1.00 parts per 100 parts of the total amount of alkoxysilanes. The co-hydrolysis reaction may be performed at 60° C. to 80° C.

Each of the alkoxysilanes in the co-hydrolysis may be employed in such an amount that the amount of the trialkoxysilane having the formula $R^{15}Si(OR^{16})_3$ is 50 to 75 mole %, alternatively 55 to 70 mole % based on the total moles of alkoxysilanes (trialkoxysilane and acryloxy functional trialkoxysilane) used.

Films may be produced from the acrylic functional silicone resin by applying the resin to a substrate and thereafter curing. The resulting films may have a thickness of 1-10 μm.

Component (b) Photoinitiator

The photopatternable silicone resin composition further comprises a photoinitiator that allows the photopatternable silicone resin composition to be photopatterned. Examples of the photoinitiator include, but are not limited to, alpha-hydroxy ketone; phenylglyoxylate; benzildimethyl-ketal; alpha-aminoketone; mono acyl phosphine; bis acyl phosphine; benzoin ether; benzoin isobutyl ether; benzoin isopropyl ether; benzophenone; benzoylbenzoic acid; methyl benzoylbenzoate; 4-benzoyl-4'-methyldiphenyl sulfide; benzylmethylketal; 2-n-butoxyethyl-4-dimethylaminobenzoate; 2-chlorothioxanthone; 2,4-diethylthioxanthanone; 1-hydroxy-cyclohexyl-phenyl-ketone (IRGACURE® 184 from Ciba-Geigy Corporation of Tarrytown, N.Y., U.S.A.), methylbenzoylformate; phenyl bis(2,4,6-trimethyl benzoyl)-phosphine oxide (IRGACURE® 819 from Ciba-Geigy Corporation of Tarrytown, N.Y., U.S.A.); and combinations thereof. The amount photoinitiator used may be 0.1 to 20 wt %, alternatively 1 to 10% based on the weight of the composition.

The photopatternable silicone resin composition may further comprise one or more optional components, such as components (D)-(I), described above.

Methods

This invention relates to a method comprising:
(1) applying a photopatternable silicone composition, such as a photopatternable silicone composition described above, to a surface in a sensing device to form a film;
(2) photopatterning the film by a process comprising exposing the film to radiation through a photomask without using a photoresist to produce an exposed film;
(3) removing regions of the non-exposed film with a developing solvent to form a patterned film; and
optionally (4) heating the patterned film.

The method may be used to form a permselective layer or an analyte attenuation layer, or both, in the sensing device.

Specific methods for application of photopatternable silicone composition to the surface in the sensing device include, but are not limited to, spin coating, extrusion coating, dip coating, spray coating, flow coating, micro-dispensing, and screen-printing. Alternatively, the photopatternable silicone composition is applied by spin coating. When a vehicle is used, the vehicle is allowed to evaporate from the surface in the sensing device during step (1) or after step (1), or both. Any suitable means for evaporation may be used such as air-drying by exposure to an ambient environment, by the application of vacuum, or mild heat or during the early stages of the curing process. When spin coating is used in step (1), any additional vehicle removal step is minimized because the spinning drives off the vehicle.

The film formed in step (1) is photopatterned to produce an exposed film. The film is photopatterned by a process comprising exposing the film to radiation through a photomask configured to expose certain portions of the film to radiation and prevent exposure of other portions of the film to radiation. A photoresist is not used. A light source that may be used to expose the film to radiation is a medium pressure mercury-arc lamp. The wavelength of the radiation may be 150 to 800 nanometers (nm), alternatively 250 to 450 nm. The dose of radiation may be 0.1 to 5,000 milliJoules per square centimeter (mJ/cm²), and alternatively from 200 to 1,000 mJ/cm².

Depending on the photopatternable silicone composition employed, the photopatterning process may be a negative resist process in which the exposed film comprises non-exposed regions soluble in a developing solvent and exposed regions that are substantially insoluble in the developing solvent. Alternatively, the photopatterning process may be a positive resist process in which the exposed film comprises exposed regions that are soluble in a developing solvent and non-exposed regions that are substantially insoluble in the developing solvent.

Radiation exposure may be sufficient to render the exposed regions substantially insoluble in a developing solvent and the non-exposed regions soluble in the developing solvent in the negative resist process (or vice versa in the positive resist process). Alternatively, the exposed film may optionally be heated after radiation exposure, e.g., for an amount of time such that the exposed regions are rendered substantially insoluble in the developing solvent, and the non-exposed regions are soluble in the developing solvent in the negative resist process. Whether to heat the exposed film and the exact conditions for heating depend on the type of photopatternable composition used. For example, when a photopatternable hydrosilylation curable silicone composition as described above is used in step (2), the exposed film may be heated at a temperature of 50 to 250° C. for 0.1 to 10 minutes, alternatively heated at a temperature of 100 to 200° C. for 1 to 5 minutes, alternatively heated at a temperature of 135 to 165° C. for 2 to 4 minutes. The exposed film may be heated using conventional equipment such as a hot plate or oven.

Regions of the non-exposed film, which are soluble in a developing solvent, are removed with the developing solvent to form a patterned film. In the negative resist process, the non-exposed regions are removed; and in the positive resist process, the exposed regions are removed with the developing solvent. The developing solvent may have from 3 to 20 carbon atoms. Examples of developing solvents include alcohols; ketones, such as methyl isobutyl ketone and methyl pentyl ketone; ethers, such as n-butyl ether and polyethylene glycol monomethylether; esters, such as ethyl acetate and g-butyrolactone; aliphatic hydrocarbons, such as nonane, decalin, and dodemaye; and aromatic hydrocarbons, such as mesitylene, xylene, and toluene; and combinations thereof. The developing solvent may be applied by any conventional method, including spraying, immersion, and pooling. Alternatively, the developing solvent may be applied by forming a pool of the solvent on a stationary substrate and then spin-drying the substrate. The developing solvent may be used at a temperature of room temperature to 100° C. However, the specific temperature will depend on the chemical properties of the solvent, the boiling point of the solvent, the desired rate of pattern formation, and the requisite resolution of the photo-patterning process.

The patterned film may optionally be heated after exposure to the developing solvent. Whether the patterned film is heated and the conditions for heating will depend on the type of photopatternable composition selected. For example, when the photopatternable hydrosilylation curable silicone composition described below is used, the patterned film may be heated for an amount of time to achieve maximum crosslink density in the silicone without oxidation or decomposition. The patterned film may be heated at a temperature of 50 to 300° C. for 1 to 300 minutes, alternatively heated at a temperature of 75 to 275° C., for 10 to 120 minutes, alternatively heated at a temperature of 200 to 250° C. for 20 to 60 minutes. The patterned film may be heated using conventional equipment such as a hot plate or oven.

A patterned film may also be produced by applying the photopatternable composition to a surface of a substrate to form a film, exposing a portion of the film to radiation having a wavelength of from 150 to 800 nm to produce an exposed film having non-exposed regions covering a portion of the surface and exposed regions covering the remainder of the surface, heating the exposed film for an amount of time such that the exposed regions are substantially insoluble in a developing solvent and the non-exposed regions are soluble in the developing solvent, removing the non-exposed regions of the heated film with the developing solvent to form a patterned film, and heating the patterned film to cure.

One skilled in the art would be able to select appropriate methods for applying the photopatternable silicone composition to the surface, exposure dose and time for photopatterning the film, developing solvents, and temperatures and times for heating the patterned film based on, for example, U.S. Pat. No. 6,617,674.

The method described above may be used during fabrication of a sensing device to form a permselective layer or an analyte attenuation layer, or both. For example, a sensing device fabrication may include forming a patterned film that is a permselective layer by the method described above and thereafter applying one or more additional layers over at least a portion of the patterned film. The method may further comprise: applying a biolayer over at least a portion of the patterned film, and applying an analyte attenuation layer over at least a portion of the biolayer. The method described above may be used to form a sensing device, where the method further comprises interposing an electrolyte layer between the sensing device and the patterned film.

Sensing Devices

This invention further relates to devices that can be made by the method described above. A device according to this invention comprises: (i) a substrate, (ii) a base sensor mounted to the substrate, optionally (iii) an electrolyte layer covering the base sensor and at least a portion of the substrate, (iv) a permselective layer covering at least a portion of the base sensor, optionally (v) a biolayer covering at least a portion of the permselective layer, optionally (vi) an analyte attenuation layer covering at least a portion of the biolayer, optionally (vii) a coupling means covering at least a portion of the permselective layer, where the coupling means may attach (viii) a ligand receptor or an immunreactive species as an outermost layer of the device; where the permselective layer is a cured product of a photopatternable silicone composition described above.

Alternatively, a device according to this invention may comprise: (i) a substrate, (ii) a base sensor mounted to the substrate, optionally (iii) an electrolyte layer covering the base sensor and at least a portion of the silicon substrate, (iv) a permselective layer covering at least a portion of the base sensor, (v) a biolayer covering at least a portion of the permselective layer, and (vi) an analyte attenuation layer covering at least a portion of the biolayer; where the permselective layer, the analyte attenuation layer, or both, is a cured product of a photopatternable silicone composition described above.

Suitable devices are known in the art, and are disclosed, for example in U.S. Pat. Nos. 5,063,081; 5,200,051; 5,212,050; 5,466,575; 5,554,339; 5,837,446; 5,837,454; and 6,306,594, which are hereby incorporated by reference for the purpose of disclosing suitable substrates, base sensors, electrolyte layers, biolayers, analyte attenuation layers, coupling means, and ligand receptors, and immunreactive species; and the devices in which they may be used. Devices that may be prepared according to this invention include, but are not limited to, an adenosine-5-triphosphate sensing device, a cardiac troponin 1 sensing device, a chloride ion sensing device, a creatinine sensing device, a creatine sensing device, a dioxygen sensing device, a glucose and cholesterol sensing device, a glucose sensing device, a hematocrit sensing device, a hydrogen peroxide sensing device, an ionized calcium sensing device, a lactate sensing device, a ligand/ligand receptor-based sensing device, a $PCO_2$ sensing device, a pH sensing device, a $PO_2$ sensing device, a potassium ion sensing device, a sodium ion sensing device, a urea nitrogen sensing device, a urea sensing device, and a uric acid sensing device.

FIG. 1 shows a cross section of a portion of a sensing device. The device 100 has a substrate 101, which is comprised of a silicon wafer having a silicon dioxide layer on its surface. Conducting signal lines 102 run to contact pads (not shown), which connect the sensing device 100 to external controlling electronics (not shown). Reference and counter electrodes 103 and indicator electrode 104 are mounted to the substrate 101 through the conducting signal lines 102. An electrolyte layer 105 covers the electrodes 103, 104 and portions of the substrate 101. A permselective layer 106 covers the electrolyte layer 105. A biolayer 107 covers a portion of the permselective layer 106. An AA layer 108 covers the biolayer 107.

FIG. 2 shows a cross section of a portion of an alternative sensing device. The device 200 has a substrate 201, which is comprised of a silicon wafer having a silicon dioxide layer on its surface. Conducting signal lines 202 run to contact pads (not shown), which connect the sensing device 200 to external controlling electronics (not shown). Reference and counter electrodes 203 and indicator electrode 204 are mounted to the substrate 201 through the conducting signal lines 202. An electrolyte layer 205 covers the electrodes 203, 204 and portions of the substrate 201. A permselective layer 206 covers the electrolyte layer 205. Coupling means 207 are mounted to the surface of the permselective layer 206. The coupling means have immobilized ligand receptors 208 on the outermost surface of the device 200.

EXAMPLES

These examples are intended to illustrate the invention to one of ordinary skill in the art and are should not be interpreted as limiting the scope of the invention set forth in the claims.

Example 1

A sample is prepared by combining 30% TPhTMethacrylate silicone resin, 68% PGMEA solvent, and 2% IRGACURE® 819. The sample is spin coated as a 1 micrometer (μm) thick film onto a silicon wafer. The film is exposed to 1000 milliJoules per square centimeter ($mJ/cm^2$) broad band ultra-violet (UV) radiation through a photomask and immediately developed with mesitylene solvent. The resulting negative image of the photomask is etched into the resulting patterned film.

Example 2

A sample is prepared by combining 71% vinyl functional silicone resin and 29% SiH functional polydimethyl siloxane dissolved in heptanes. To this is added 10 parts per million (ppm) platinum acetylacetonate. The sample is spin coated onto a silicon wafer. The film is then exposed through a photomask to 200 $mJ/cm^2$ of UV radiation and afterward heated to 140° C. for 10 minutes. The resulting exposed film is washed with toluene to remove the non-crosslinked portion of the film. This results in a negative image of the photomask pattern etched into the resulting patterned film.

INDUSTRIAL APPLICABILITY

This invention may be used to prepare sensing devices using wafer level packaging methods. The method of this invention may be used to form a permselective layer, an analyte attenuation layer, or both in a sensing device. Permselective layers may be formed in the devices prior to dicing the wafer, which may form the substrate.

DRAWINGS

Figure 1:
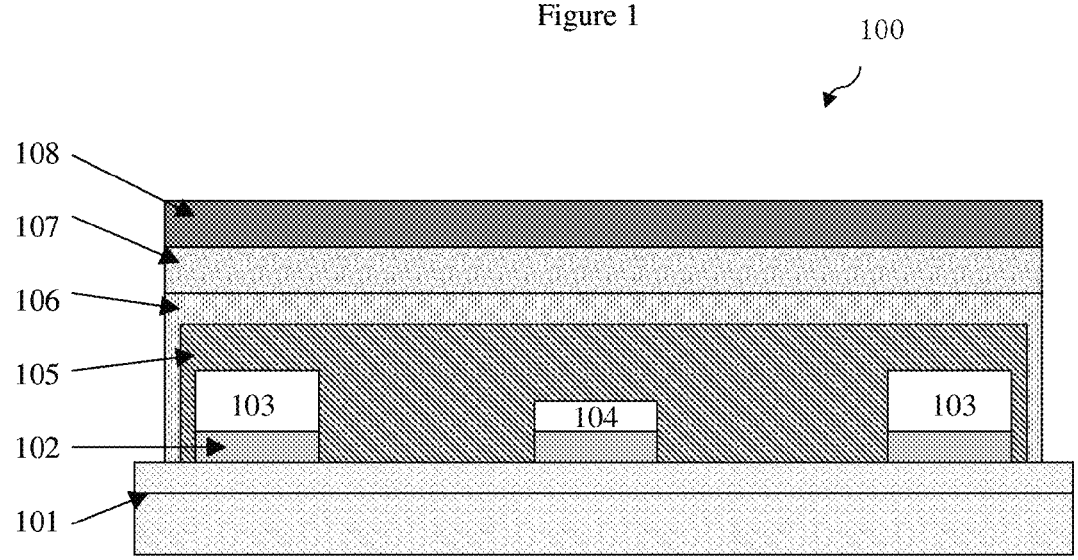
FIG. 1 shows a cross section of a portion of a sensing device.
Figure 2:
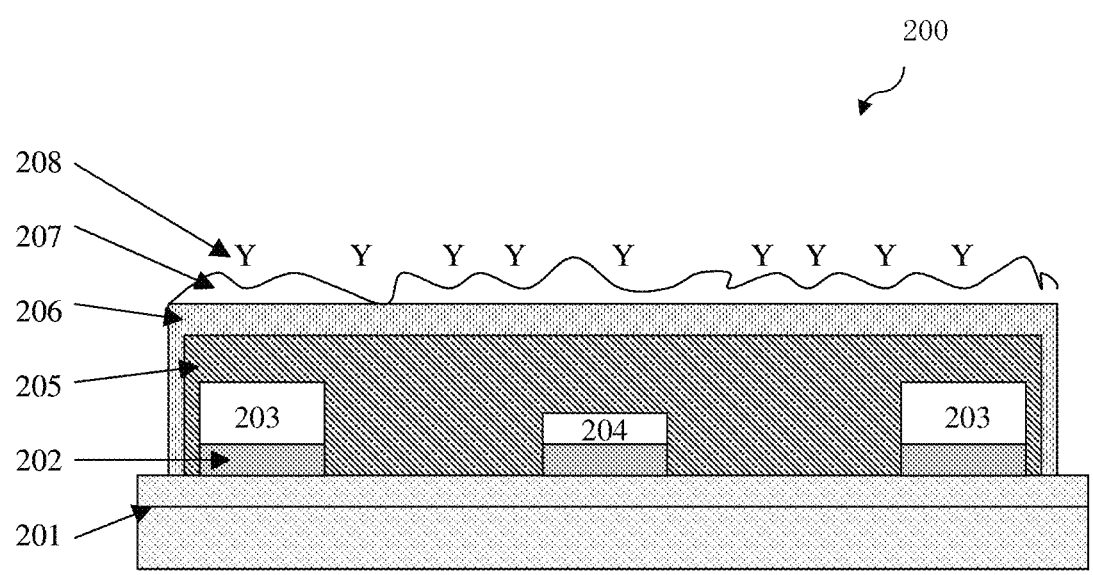
FIG. 2 shows a cross section of a portion of an alternative sensing device.

100 device
101 substrate
102 conducting signal line
103 reference and counter electrode
104 indicator electrode
105 electrolyte layer
106 permselective layer
107 biolayer
108 analyte attenuation layer
200 device
201 substrate
202 conducting signal line
203 reference and counter electrode
204 indicator electrode
205 electrolyte layer
206 permselective layer
207 coupling means
208 immobilized ligand receptors

The invention claimed is:

1. A method comprising:
   (1) applying a photopatternable semi-permeable silicone resin composition to a surface in a sensing device to form a film, wherein the sensing device comprises a silicon wafer having a silicon dioxide layer on its surface,
   (2) photopatterning the film by a process comprising exposing the film to radiation through a photomask without using a photoresist to produce an exposed film;
   (3) removing regions of the non-exposed film with a developing solvent to form a patterned semi-permeable film; and
   (4) heating the patterned film,
   wherein the photopatternable semi-permeable silicone resin composition comprises:
      (a) a curable silicone resin and
      (b) a photoinitiator,
   wherein the curable silicone resin is selected from an acrylic functional silicone resin of the formula

where each $R^{13}$ is independently a hydrogen atom or methyl group, each $R^{14}$ is independently a hydrocarbylene group having 1 to 8 carbon atoms, each $R^{15}$ is independently an alkyl, cyclic alkyl, aryl or alkenyl group having 1 to 8 carbon atoms, wherein h satisfies the inequality $0.05<h<0.95$, wherein i satisfies the inequality $0.05<i<0.95$, $h+i=1$, and j is a value sufficient to give the acrylic functional silicone resin a weight average molecular weight (Mw) of 3,000 to 100,000 grams per mole in terms of polystyrene by gel permeation chromatography, a vinyl ether functional silicone resin, an epoxy functional silicone resin, or a combination thereof.

2. The method of claim 1, further comprising applying a biolayer over at least a portion of the patterned film.

3. The method of claim 2, further comprising applying an analyte attenuation layer over at least a portion of the biolayer.

4. A method comprising:
(1) applying a photopatternable silicone resin composition to a surface in a sensing device to form a film, wherein the sensing device comprises a silicon wafer having a silicon dioxide layer on its surface,
(2) photopatterning the film by a process comprising exposing the film to radiation through a photomask without using a photoresist to produce an exposed film;
(3) removing regions of the non-exposed film with a developing solvent to form a patterned film; and
(4) heating the patterned film,
where the photopatternable silicone resin composition comprises:
(a) a curable silicone resin and
(b) a photoinitiator,
wherein the curable silicone resin is selected from an acrylic functional silicone resin, of the formula $\{[(CH_2\!=\!CR^{13}COOR^{14})SiO_{3/2}]_h[R^{15}SiO_{3/2}]_i\}_j$, where each $R^{13}$ is independently a hydrogen atom or methyl group, each $R^{14}$ is independently a hydrocarbylene group having 1 to 8 carbon atoms, each $R^{15}$ is independently an alkyl, cyclic alkyl, aryl or alkenyl group having 1 to 8 carbon atoms, wherein h satisfies the inequality $0.05<h<0.95$, wherein i satisfies the inequality $0.05<i<0.95$, $h+i=1$, and j is a value sufficient to give the acrylic functional silicone resin a weight average molecular weight (Mw) of 3,000 to 100,000 grams per mole in terms of polystyrene by gel permeation chromatography, a vinyl ether functional silicone resin, an epoxy functional silicone resin, or a combination thereof,
optionally (c) an inhibitor,
optionally (d) a filler,
optionally (e) a treating agent for the filler,
optionally (f) a vehicle,
optionally (g) a spacer,
optionally (h) an adhesion promoter,
optionally (i) a surfactant,
optionally (j) a photosensitizer, and
optionally (k) a colorant.

5. The method of claim 1 or 4, where the surface comprises a wafer on which a first structure comprising a base sensor is mounted.

6. The method of claim 5, further comprising interposing an electrolyte layer between the base sensor and the patterned film.

* * * * *